United States Patent [19]

Kawaoka et al.

[11] 4,061,646

[45] Dec. 6, 1977

[54] PROCESS FOR PURIFICATION OF CRUDE 2-MERCAPTOBENZOTHIAZOLE

[75] Inventors: Yutaka Kawaoka, Yanai; Tatsuo Kifune, Yamaguchi; Masahiko Teshima, Yamaguchi; Tatsuya Koizumi, Yamaguchi, all of Japan

[73] Assignee: Sanshin Kagaku Kogyo Company, Limited, Yamaguchi, Japan

[21] Appl. No.: 701,227

[22] Filed: June 30, 1976

[30] Foreign Application Priority Data

Jan. 14, 1976   Japan .................................... 51-3056

[51] Int. Cl.² .......................................... C07D 277/72
[52] U.S. Cl. .................................................... 260/306
[58] Field of Search ......................................... 260/306

[56] References Cited

U.S. PATENT DOCUMENTS

| | | | |
|---|---|---|---|
| 2,090,233 | 8/1937 | Roberts | 260/306 |
| 3,031,073 | 4/1962 | Szlatinay | 260/306 |

*Primary Examiner*—Richard J. Gallagher
*Attorney, Agent, or Firm*—Oblon, Fisher, Spivak, McClelland & Maier

[57] ABSTRACT

Crude 2-mercaptobenzothiazole is purified by preparing a crude, liquid 2-mercaptobenzothiazole by reacting aniline, carbon disulfide and sulfur under elevated pressure at high temperatures; extracting said crude, liquid 2-mercaptobenzothiazole in the molten state with cold carbon disulfide by liquid-liquid extraction thereby forming a slurry of 2-mercaptobenzothiazole crystals; and filtering and drying said crystals.

6 Claims, No Drawings

PROCESS FOR PURIFICATION OF CRUDE 2-MERCAPTOBENZOTHIAZOLE

BACKGROUND OF THE INVENTION

1. Field of the Invention

The present invention relates to a process for the purification of crude 2-mercaptobenzothiazole.

2. Description of the Prior Art

2-Mercaptobenzothiazole and its derivatives such as dibenzothiazole disulfide, cyclohexylbenzothiazylsulfenamide, N-oxydiethylenebenzothiazyl-sulfenamide, zinc salts of 2-mercaptobenzothiazole, diethylbenzothiazyl sulfenamide and the cyclohexylamine salt of 2-mercaptobenzothiazole which are generally referred to in the vulcanization art as the thiazole series of accelerators are important vulcanization accelerators which are used in large quantities in the natural and synthetic rubber industry. Moreover, many patents and literature references have been published on the preparation and purification of 2-mercaptobenzothiazole.

It is well known that in the conventional Kelly process for preparing 2-mercaptobenzothiazole by the reaction of aniline, carbon disulfide and sulfur under elevated pressure at high temperatures, the product contains not only by-products such as benzothiazole, anilinobenzothiazole, phenylisothiocyanate, benzoisonitrile and a tarry material of unknown composition, but also unreacted sulfur, aniline and carbon disulfide. These by-products and unreacted materials are usually removed from the product by dissolving it in a dilute solution of caustic soda, and filtering the solution after partial oxidation and acidification if necessary. However, in this process a large amount of water is used to dilute the caustic soda solution, it takes many hours to remove suspended substances from the solution to form a clear solution of the salt of 2-mercaptobenzothiazole sodium, and the tarry matter which separates from the solution is so dirty and foul smelling that it is very troublesome in handling.

One effort to improve the purification of crude 2-mercaptobenzothiazole involved the extraction of the reaction products with carbon disulfide. The method, as disclosed in Canadian Pat. No. 448,209, is based on the fact that all of the above described impurities are very soluble in carbon disulfide, while 2-mercaptobenzothiazole is less soluble. However, this method must be conducted in apparatus which is relatively small compared to the apparatus employed in the caustic soda process. Moreover, the technique is also used as a method for treating solid crude 2-mercaptobenzothiazole. The technique, has the disadvantage of being more expensive than the conventional liquid extraction process since it must be conducted in batch type systems requiring much labor and time. In addition, the method is detrimental to human health because of gases evolved in the extraction of crude 2-mercaptobenzothiazole which include small amounts of hydrogen sulfide. Moreover, as is evident from the disclosure of U.S. Pat. No. 2,090,233, in the extraction of solid, crude 2-mercaptobenzothiazole with carbon disulfide, a large amount of solvent is required to achieve the desired purity level of 97.5 to 99.5%, since the extraction process must be repeated two or three time or more to completely remove the tarry impurities.

In summary, the prior art procedures for purifying crude 2-mercaptobenzothiazole have many deficiencies in that a large amount of solvent or water is consumed, it is difficult and troublesome to separate and handle the tarry by-products, much labor and time are required and they can be detrimental to human health.

SUMMARY OF THE INVENTION

Accordingly, one object of the present invention is to provide an improved process for purifying crude 2-mercaptobenzothiazole, which has none of the above described drawbacks.

Briefly, this object and other objects can be attained by extracting liquid, crude 2-mercaptobenzothiazole in the molten state immediately after its preparation by the reaction of aniline, carbon disulfide and sulfur with cold carbon disulfide by liquid-liquid extraction. More particularly, the objects of the invention can be attained by quenching crude 2-mercaptobenzothiazole in the molten state immediately after its preparation by the reaction of aniline, carbon disulfide and sulfur under elevated pressure at high temperatures by pouring the crude, liquid 2-mercaptobenzothiazole into cold carbon disulfide, and filtering and drying the resulting fine crystals of 2-mercaptobenzothiazole. The basic discovery of the invention is that when liquid 2-mercaptobenzothiazole is poured into cold carbon disulfide, it instantaneously precipitates as fine crystals from solution.

DETAILED DESCRIPTION OF THE PREFERRED EMBODIMENTS

Immediately after its preparation by the conventional reaction of aniline, carbon disulfide and sulfur at an elevated pressure and high temperature, crude 2-mercaptobenzothiazole is obtained in the molten state at about 170° C and is introduced into an extractor where it is contacted with carbon disulfide which is circulated in the extractor and maintained at a temperature below the boiling point of carbon disulfide, preferably 10° to 20° C. The amount of carbon disulfide employed is 2 to 20 times the amount of crude 2-mercaptobenzothiazole, preferably 5 to 10 times. 2-Mercaptobenzothiazole is quenched by carbon disulfide and is instantaneously precipitated as fine crystals. Simultaneously, all impurities such as benzothiazole, phenylisothiocyanate and all tarry by-products present in the crude 2-mercaptobenzothiazole are completely dissolved in carbon disulfide and extracted. Then, the fine, precipitated crystals are separated from the carbon disulfide solution by filtration and dried. The 2-mercaptobenzothiazole product obtained by this procedure has a purity above 99.5%.

The present invention has many advantages as follows:

1. The continuous extraction of crude 2-mercaptobenzothiazole with carbon disulfide can be easily and automatically conducted because crude 2-mercaptobenzothiazole is liquid in the molten state which renders it amenable to liquid-liquid extraction.

2. The pulverization step, which is necessary for solid, crude 2-mercaptobenzothiazole prior to extraction in the conventional procedure, is not necessary.

3. The extraction procedure is a flash extraction procedure which can be instantaneously run.

4. Since all the process steps can be conducted in an enclosed vessel, the process is not foul smelling nor detrimental to human health.

5. A high purity 2-mercaptobenzothiazole product can be obtained by using only a small amount of carbon disulfide since additional washing with carbon disulfide is not necessary.

6. The amount of tarry by-product is very small because the contents of the reaction vessel are not subjected to air oxidation since all the processes are conducted in an enclosed vessel excluding air. Moreover, little time is available to allow any side reactions to occur between intermediates which side reactions often occur after the removal of hydrogen sulfide which acts as a reducing agent and maintains chemical equilibrium.

7. The present process also has the advantage that the noxious tarry by-product is produced in only small amounts. In addition, the waste water containing various organic and inorganic substances which is produced in the conventional purification process from the caustic soda washing solution is not produced, and, therefore, the yield of product is good.

8. The yield of product is also highly stable since the present process does not involve any complicated reactions.

9. Unreacted materials and by-products from the preparation reaction of 2-mercaptobenzothiazole can be recovered from the extraction solution and reused.

10. Water resources can be economized.

In the extraction process of the present invention all impurities such as benzothiazole, phenylisothiocyanate and tarry matter present in the crude 2-mercaptobenzothiazole are completely and instantaneously dissolved in the carbon disulfide. The 2-mercaptobenzothiazole product, which is insoluble in carbon disulfide, can be obtained as a fine crystalline precipitate having a purity above 99.5%.

Having generally described the invention, a more complete understanding can be obtained by reference to certain specific examples, which are provided herein for purposes of illustration only and are not intended to be limiting unless otherwise specified.

EXAMPLE 1

A 500kg amount of aniline, 172kg of sulfur and 445 kg of carbon disulfide were charged into a continuous type of autoclave and reacted at 220° C under a pressure of 110kg/cm$^2$ for about 50 minutes. The reaction product was introduced into a gas-liquid separating tank whereby hydrogen sulfide was removed from the top of the tank, and 200 kg of liquid, crude 2-mercaptobenzothiazole were obtained. The crude product was introduced into the bottom of an extracting tower in which 500kg of carbon disulfide at 10° C were continuously circulated. The liquid, crude 2-mercaptobenzothiazole flowing upward in the tower was contacted with carbon disulfide flowing downward thereby forming a slurry of fine crystals of 2-mercaptobenzothiazole in carbon disulfide. The slurry was introduced into a filter to separate the precipitated crystals by a quantitative pump from carbon disulfide whereby powdered 2-mercaptobenzothiazole was obtained. The powder was dried in a dryer to recover solvent therefrom whereby 174kg of a light yellowish-white powder of 2-mercaptobenzothiazole of 99.5% purity and having a melting point of 172° to 175° C were obtained.

What is claimed is:

1. A process for purifying crude 2-mercaptobenzothiazole, which comprises:
    preparing a crude, molten 2-mercaptobenzothiazole by reacting aniline, carbon disulfide and sulfur under elevated pressure at high temperatures;
    immediately quenching said molten, crude 2-mercaptobenzothiazole after its preparation by pouring said molten, crude 2-mercaptobenzothiazole into cold carbon disulfide thereby forming a slurry of 2-mercaptobenzothiazole crystals; and
    filtering and drying said crystals of 2-mercaptobenzothiazole.

2. The method of claim 1, wherein the temperature of said carbon disulfide ranges from 10° to 20° C.

3. The method of claim 1, wherein the amount of said carbon disulfide employed ranges from 2 to 20 times the amount of said crude 2-mercaptobenzothiazole.

4. The method of claim 1, wherein unreacted materials and by-products from said reaction are recovered from the carbon disulfide quench solution and reused for the preparation of 2-mercaptobenzothiazole.

5. The method of claim 1, wherein said quenching step is accomplished by liquid-liquid extraction of said crude, molten 2-mercaptobenzothiazole by cold carbon disulfide.

6. The method of claim 5, wherein said extraction is conducted by continuously circulating carbon disulfide.

* * * * *